US006648854B1

(12) United States Patent
Patterson et al.

(10) Patent No.: US 6,648,854 B1
(45) Date of Patent: Nov. 18, 2003

(54) SINGLE LUMEN BALLOON-TIPPED MICRO CATHETER WITH REINFORCED SHAFT

(75) Inventors: Marlowe E. Patterson, Milpitas, CA (US); Thomas Yung-Hui Chien, San Jose, CA (US); Hanh Doan, Milpitas, CA (US); Hong Doan, San Jose, CA (US); Huey Quoc Chan, San Jose, CA (US); Henry Nita, Redwood Shores, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/311,446

(22) Filed: May 14, 1999

(51) Int. Cl.[7] ............................................. A61M 37/00
(52) U.S. Cl. ..................... 604/96.01; 604/524; 604/527
(58) Field of Search ............................. 604/96.01, 104, 604/164.01–164.03, 164.13, 170.01–170.03, 264, 523–529

(56) References Cited

U.S. PATENT DOCUMENTS

| 1,878,671 A | 9/1932 | Cantor |
| 1,920,006 A | 7/1933 | Dozier |
| 2,211,975 A | 8/1940 | Hendrickson ............... 128/349 |
| 2,437,542 A | 3/1948 | Krippendorf ................. 128/349 |
| 3,174,851 A | 3/1965 | Buehler et al. ................ 75/170 |
| 3,351,463 A | 11/1967 | Rozner et al. ................. 75/170 |
| 3,416,531 A | 12/1968 | Edwards ...................... 128/348 |
| 3,467,101 A | 9/1969 | Fogarty et al. ............. 128/348 |
| 3,753,700 A | 8/1973 | Harrison et al. ............ 75/175.5 |
| 3,757,768 A | 9/1973 | Kline ........................ 128/2 M |
| 3,850,720 A | * 11/1974 | Collins ........................ 156/155 |
| 3,924,632 A | 12/1975 | Cook .......................... 128/348 |
| 4,187,960 A | * 2/1980 | Bonk .......................... 222/107 |
| 4,307,722 A | 12/1981 | Evans ......................... 128/344 |
| 4,323,071 A | 4/1982 | Simpson et al. ............. 128/343 |

(List continued on next page.)

FOREIGN PATENT DOCUMENTS

| DE | 32 42 449 A1 | 5/1983 |
| DE | 36 42 107 A1 | 6/1987 |
| EP | 0 184 314 A1 | 6/1986 |
| EP | 0 098 100 B1 | 10/1986 |
| EP | 0 421 650 A1 | 4/1991 |
| EP | 0 368 931 B1 | 10/1993 |
| EP | 0 597 465 A1 | 5/1994 |
| EP | 0 570 517 B1 | 8/1996 |
| FR | 2 613 231 A1 | 10/1988 |
| WO | WO 89/01352 | 2/1989 |
| WO | WO 92/07507 | 5/1992 |
| WO | WO 92/13589 | 8/1992 |
| WO | WO 93/05842 | 4/1993 |
| WO | WO 93/07925 | 4/1993 |
| WO | WO 93/15785 | 8/1993 |
| WO | WO 93/17750 | 9/1993 |
| WO | WO 94/11047 | 5/1994 |
| WO | WO 94/27668 | 12/1994 |
| WO | WO 96/30074 | 10/1996 |
| WO | WO 97/17998 | 5/1997 |

OTHER PUBLICATIONS

US 5,171,298, 12/1992, Walker et al. (withdrawn)

Technical Fact Sheet: ChronoPrene, dated on or before May 14, 1999, 2 sheets.

*Primary Examiner*—Long V. Le
*Assistant Examiner*—Ann Y. Lam
(74) *Attorney, Agent, or Firm*—Crompton, Seager & Tufte, LLC (57) ABSTRACT

A single lumen balloon-tipped micro catheter, wherein the distal portion of the shaft is reinforced and extends into the balloon to eliminate abrupt transitions in stiffness in the balloon region. The balloon may be formed of a thermoplastic polyisoprene rubber such as hydrogenated polyisoprene which has superior performance and manufacturing attributes.

19 Claims, 4 Drawing Sheets

U.S. PATENT DOCUMENTS

| | | | | |
|---|---|---|---|---|
| 4,411,055 A | | 10/1983 | Simpson et al. | 29/447 |
| 4,413,989 A | | 11/1983 | Schjeldahl et al. | 604/96 |
| 4,425,919 A | | 1/1984 | Alston, Jr. et al. | 128/658 |
| 4,430,083 A | | 2/1984 | Ganz et al. | 604/283 |
| 4,448,195 A | | 5/1984 | LeVeen et al. | 128/344 |
| 4,484,586 A | | 11/1984 | McMickle et al. | 128/786 |
| 4,516,972 A | | 5/1985 | Samson | 604/282 |
| 4,571,240 A | | 2/1986 | Samson et al. | 604/96 |
| 4,606,347 A | | 8/1986 | Fogarty et al. | 128/344 |
| 4,646,719 A | | 3/1987 | Neuman et al. | 128/1 |
| 4,657,024 A | | 4/1987 | Coneys | 128/658 |
| 4,676,229 A | | 6/1987 | Krasnicki et al. | 128/4 |
| 4,702,252 A | * | 10/1987 | Brooks et al. | 128/344 |
| 4,706,670 A | | 11/1987 | Andersen et al. | 128/344 |
| 4,737,153 A | | 4/1988 | Shimamura et al. | 604/282 |
| 4,806,182 A | | 2/1989 | Rydell et al. | 156/211 |
| 4,817,613 A | | 4/1989 | Jaraczewski et al. | 128/658 |
| 4,832,681 A | | 5/1989 | Lenck | 600/34 |
| 4,848,344 A | | 7/1989 | Sos et al. | 128/344 |
| 4,884,573 A | | 12/1989 | Wijay et al. | 128/344 |
| 4,892,519 A | | 1/1990 | Songer et al. | 604/96 |
| 4,899,787 A | | 2/1990 | Ouchi et al. | 138/131 |
| 4,917,666 A | | 4/1990 | Solar et al. | 604/95 |
| 4,921,483 A | | 5/1990 | Wijay et al. | 604/96 |
| 4,944,740 A | | 7/1990 | Buchbinder et al. | 606/194 |
| 4,960,410 A | | 10/1990 | Pinchuk | 604/96 |
| 4,976,720 A | | 12/1990 | Machold et al. | 606/194 |
| 4,981,478 A | | 1/1991 | Evard et al. | 604/282 |
| 4,985,022 A | | 1/1991 | Fearnot et al. | 604/282 |
| 4,994,032 A | | 2/1991 | Sugiyama et al. | 604/96 |
| 4,994,069 A | | 2/1991 | Ritchart et al. | 606/191 |
| 5,004,461 A | | 4/1991 | Wilson | 604/265 |
| 5,017,259 A | | 5/1991 | Kohsai | 156/294 |
| 5,019,057 A | | 5/1991 | Truckai | 604/282 |
| 5,032,113 A | | 7/1991 | Burns | 604/96 |
| 5,035,705 A | | 7/1991 | Burns | 606/194 |
| 5,037,404 A | | 8/1991 | Gold et al. | 604/282 |
| 5,057,092 A | | 10/1991 | Webster, Jr. | 604/282 |
| 5,069,674 A | | 12/1991 | Fearnot et al. | 604/282 |
| 5,085,636 A | | 2/1992 | Burns | 604/99 |
| 5,100,381 A | | 3/1992 | Burns | 604/96 |
| 4,813,934 A | | 5/1992 | Engelson et al. | 604/99 |
| 5,112,304 A | | 5/1992 | Barlow et al. | 604/96 |
| 5,122,136 A | | 6/1992 | Guglielmi et al. | 606/32 |
| 5,135,494 A | | 8/1992 | Engelson et al. | 604/99 |
| 5,141,518 A | | 8/1992 | Hess et al. | 606/194 |
| 5,171,221 A | | 12/1992 | Samson | 604/96 |
| 5,171,297 A | | 12/1992 | Barlow et al. | 604/96 |
| 5,176,660 A | | 1/1993 | Truckai | 604/282 |
| 5,176,661 A | | 1/1993 | Evard et al. | 604/282 |
| 5,176,698 A | | 1/1993 | Burns et al. | 606/192 |
| 5,178,158 A | | 1/1993 | de Toledo | 128/772 |
| 5,180,376 A | | 1/1993 | Fischell | 604/282 |
| 5,184,627 A | | 2/1993 | de Toledo | 128/772 |
| 5,192,295 A | | 3/1993 | Danforth et al. | 606/194 |
| 5,207,229 A | | 5/1993 | Winters | 168/772 |
| 5,217,434 A | | 6/1993 | Arney | 604/99 |
| 5,217,482 A | | 6/1993 | Keith | 606/194 |
| 5,221,260 A | | 6/1993 | Burns et al. | 604/99 |
| 5,221,261 A | | 6/1993 | Termin et al. | 604/104 |
| 5,222,949 A | | 6/1993 | Kaldany | 604/282 |
| 5,248,305 A | | 9/1993 | Zdrahala | 604/280 |
| 5,250,034 A | | 10/1993 | Appling et al. | 604/164 |
| 5,254,107 A | | 10/1993 | Soltesz | 604/282 |
| 5,256,144 A | | 10/1993 | Kraus et al. | 604/96 |
| 5,259,839 A | | 11/1993 | Burns | 604/99 |
| 5,290,230 A | * | 3/1994 | Ainsworth et al. | 604/96 |
| 5,304,198 A | | 4/1994 | Samson | 606/194 |
| 5,313,967 A | | 5/1994 | Lieber et al. | 128/772 |
| 5,318,529 A | | 6/1994 | Kontos | 604/96 |
| 5,324,259 A | | 6/1994 | Taylor et al. | 604/96 |
| 5,324,263 A | | 6/1994 | Kraus et al. | 604/96 |
| 5,338,295 A | | 8/1994 | Cornelius et al. | 604/96 |
| 5,338,299 A | | 8/1994 | Barlow | 604/96 |
| 5,348,537 A | * | 9/1994 | Wiesner et al. | 604/96 |
| 5,354,295 A | | 10/1994 | Guglielmi et al. | 606/32 |
| 5,364,354 A | | 11/1994 | Walker et al. | 604/96 |
| 5,370,615 A | | 12/1994 | Johnson | 604/96 |
| 5,378,236 A | * | 1/1995 | Seifert | 604/96 |
| 5,378,238 A | | 1/1995 | Peters et al. | 604/99 |
| 5,380,282 A | | 1/1995 | Burns | 604/96 |
| 5,380,304 A | | 1/1995 | Parker | 604/282 |
| 5,397,305 A | | 3/1995 | Kawula et al. | 604/96 |
| 5,405,338 A | | 4/1995 | Kranys | 604/282 |
| 5,425,712 A | | 6/1995 | Goodin | 604/96 |
| 5,429,604 A | | 7/1995 | Hammersmark et al. | 604/95 |
| 5,437,632 A | | 8/1995 | Engelson | 604/53 |
| 5,451,209 A | | 9/1995 | Ainsworth et al. | 604/96 |
| 4,739,768 A | | 10/1995 | Engelson | 128/658 |
| 5,454,788 A | | 10/1995 | Walker et al. | 604/96 |
| 5,454,789 A | | 10/1995 | Burns et al. | 604/99 |
| 5,454,795 A | | 10/1995 | Samson | 604/282 |
| 5,460,608 A | | 10/1995 | Lodin et al. | 604/96 |
| 5,476,477 A | | 12/1995 | Burns | 606/194 |
| 5,484,408 A | | 1/1996 | Burns | 604/96 |
| 5,492,532 A | | 2/1996 | Ryans et al. | 604/96 |
| 5,499,973 A | | 3/1996 | Saab | 604/96 |
| 5,499,995 A | | 3/1996 | Teirstein | 606/192 |
| 5,531,689 A | | 7/1996 | Burns et al. | 604/99 |
| 5,531,721 A | | 7/1996 | Pepin et al. | 604/282 |
| 5,538,510 A | | 7/1996 | Fontirroche et al. | 604/265 |
| 5,538,513 A | | 7/1996 | Okajima | 604/282 |
| 5,554,121 A | | 9/1996 | Ainsworth et al. | 604/96 |
| 5,569,201 A | | 10/1996 | Burns | 604/96 |
| 5,569,220 A | | 10/1996 | Webster, Jr. | 604/282 |
| 5,599,325 A | | 2/1997 | Ju et al. | 604/282 |
| 5,643,209 A | | 7/1997 | Fugoso et al. | 604/96 |
| 5,658,264 A | | 8/1997 | Samson | 604/282 |
| 5,683,410 A | | 11/1997 | Samson | 606/194 |
| 5,702,373 A | | 12/1997 | Samson | 604/282 |
| 5,713,854 A | * | 2/1998 | Inderbitzen et al. | 604/53 |
| 5,718,711 A | | 2/1998 | Berenstein et al. | 606/191 |
| 5,722,424 A | * | 3/1998 | Engelson | 128/772 |
| 5,725,513 A | | 3/1998 | Ju et al. | 604/280 |
| 5,728,063 A | | 3/1998 | Preissman et al. | 604/96 |
| 5,728,066 A | | 3/1998 | Daneshvar | 604/96 |
| 5,730,734 A | | 3/1998 | Adams et al. | 604/280 |
| 5,731,087 A | | 3/1998 | Fan et al. | 428/412 |
| 5,209,728 A | | 4/1998 | Kraus et al. | 604/96 |
| 5,749,894 A | | 5/1998 | Engelson | 606/213 |
| 5,752,934 A | | 5/1998 | Campbell et al. | 604/96 |
| 5,759,173 A | | 6/1998 | Preissman et al. | 604/96 |
| 5,769,796 A | | 6/1998 | Palermo et al. | 600/585 |
| 5,769,819 A | | 6/1998 | Schwab et al. | 604/103 |
| 5,769,821 A | | 6/1998 | Abrahamson et al. | 604/104 |
| 5,772,681 A | | 6/1998 | Leoni | 606/192 |
| 5,776,099 A | | 7/1998 | Tremulis | 604/96 |
| 5,779,730 A | | 7/1998 | Miller | 606/192 |
| 5,782,811 A | | 7/1998 | Samson et al. | 604/282 |
| 5,783,633 A | | 7/1998 | Sperling et al. | 525/131 |
| 5,800,391 A | | 9/1998 | Kontos | 604/96 |
| 5,820,594 A | | 10/1998 | Fontirroche et al. | 604/96 |
| 5,820,613 A | | 10/1998 | Van Werven-raNsen et al. | 604/282 |
| 5,823,992 A | | 10/1998 | Salmon et al. | 604/53 |
| 5,827,201 A | | 10/1998 | Samson et al. | 600/585 |
| 5,827,225 A | | 10/1998 | Ma Schwab | 604/96 |
| 5,836,912 A | | 11/1998 | Kusleika | 604/96 |

| | | | |
|---|---|---|---|
| 5,843,092 A | 12/1998 | Heller et al. | 606/108 |
| 5,891,112 A | 4/1999 | Samson | 604/282 |
| 5,891,114 A | 4/1999 | Chien et al. | 604/282 |
| 5,938,645 A * | 8/1999 | Gordon | 604/264 |
| 6,010,521 A * | 1/2000 | Lee et al. | 606/194 |
| 6,186,978 B1 * | 2/2001 | Samson et al. | 604/96.01 |

* cited by examiner

SINGLE LUMEN BALLOON-TIPPED MICRO CATHETER WITH REINFORCED SHAFT

FIELD OF THE INVENTION

The present invention generally relates to intravascular catheters. Specifically, the present invention relates to intravascular balloon catheters such as single lumen balloon-tipped micro catheters.

BACKGROUND OF THE INVENTION

Intravascular balloon catheters are used is a wide variety of medical procedures to diagnose and treat vascular abnormalities such as aneurysms, stenotic lesions, intracranial shunts, etc. Such balloon catheters may be used for purposes of dilation, occlusion, flow control or tissue reformation.

Intravascular balloon catheters are typically navigated through the vasculature to the desired treatment site using a guide wire. The guide wire is insertable into the catheter and may be torqued to steer the distal end thereof and thereby direct the catheter into the desired vascular passage. Once in the desired position, the balloon may be inflated to treat the vascular abnormality. Such balloon catheters usually include a guide wire lumen to accommodate the guide wire in addition to a separate inflation lumen for inflating and deflating the balloon.

The provision of a guide wire lumen separate from an inflation lumen dictates a catheter profile that may be too large for accessing relatively narrow vasculature often encountered, for example, in cranial applications. Accordingly, it is desirable to provide a combined guide wire lumen and inflation lumen to reduce the profile of the catheter and thereby enable access to narrow vasculature. Balloon catheters incorporating a combined guide wire lumen and inflation lumen are often referred to as "innerless" or "single lumen" balloon catheters.

A single lumen balloon catheter requires some sort of seal or valve between the guide wire and the catheter distal of the inflatable balloon. Examples of such a catheter construction may be found in U.S. Pat. No. 5,776,099 to Tremulis and commonly assigned U.S. Pat. No. 4,813,934 to Engelson et al. The seal is typically provided adjacent the distal end of the balloon and forms a close fit or an interference fit with the guide wire. Because of the close fit or interference fit, some friction between the guide wire and the seal may be encountered.

Due to the friction between the guide wire and the seal, in addition to the friction between the balloon and the vasculature, the balloon may be susceptible to longitudinal collapse. The tendency for longitudinal collapse is exasperated by the balloon structure which is usually formed of a thin flexible material.

To address the potential for longitudinal collapse, a support coil may be provided extending from the proximal end of the balloon to the distal end of the balloon adjacent the seal. The support coil provides column strength to the balloon and reduces the potential for longitudinal collapse. Examples of such support coils may be found in Engelson '934 and in Tremulis '099. The commercial embodiment of the Tremulis '099 catheter included a polymer tube in the support coil.

Although the support coil provides column strength to the balloon, the transition in flexibility from the shaft immediately proximal to the balloon to the support coil within the balloon may be fairly abrupt. The support coil is inherently flexible and the balloon is very flexible since it is formed of a thin pliable material. The shaft, by contrast, is usually less flexible to provide sufficient pushability. The result is an abrupt transition in stiffness from the relatively less flexible distal shaft portion to the relatively more flexible support coil and balloon. An abrupt transition in stiffness may translate into reduced trackability and an increased potential for kinking.

SUMMARY OF INVENTION

The present invention overcomes these disadvantages by providing a unique single lumen balloon-tipped micro catheter wherein the distal portion of the shaft is reinforced and extends into the balloon to eliminate abrupt transitions in stiffness in the balloon region. The result is a micro catheter exhibiting superior pushability, trackability, and kink resistance.

In an exemplary embodiment, the micro catheter includes an elongate shaft having a distal portion comprising a reinforcement layer disposed between two polymer layers. The elongate shaft also includes a lumen extending therethrough to accommodate a removable guide wire and to define an inflation lumen. An inflatable balloon is connected to the distal portion of the shaft such that the distal portion of the shaft extends into the interior of the balloon to thereby eliminate significant transitions in stiffness. One or more inflation ports extend through the distal portion of the shaft to provide a fluid path between the lumen of the shaft and the interior of the balloon. A seal is connected to the distal portion of the shaft distal of the inflation port to provide a fluid tight seal about a guide wire such that the balloon may be inflated via the lumen of the shaft.

The reinforcement layer in the distal portion of the shaft may comprise a braided tubular structure to impart enhanced pushability and kink resistance without compromising flexibility. With a braid reinforcement layer, the inflation ports are preferably disposed between the filaments of the braid to avoid compromising the mechanical integrity of the distal portion of the shaft. The filaments of the braid may be formed of a super elastic metal such as a nickel titanium alloy to withstand significant strains often encountered in tortuous vasculature.

One or more radiopaque marker bands may be disposed between the inner and outer polymer layers adjacent the balloon to facilitate fluoroscopic visualization. The outer surface of the catheter shaft may include a lubricious coating thereon to reduce friction between the catheter and the vasculature as the catheter is navigated therethrough. The entire outer surface of the shaft may be coated except at locations where the balloon is bonded to avoid jeopardizing bond integrity. This may be accomplished by utilizing a masking technique during the coating process.

The seal may be formed by a reduced diameter portion of the distal portion of the shaft. Preferably, the seal is sized to form an interference fit with the guide wire. The seal may be formed of a non-elastomer polymer, but operate within the elastic region of the material. Operating within the elastic region of the material allows the seal to be. formed of any suitable plastics without requiring that the material be elastomeric.

The balloon may be formed of a thermoplastic polyisoprene rubber such as hydrogenated polyisoprene, which has superior functional properties in addition to desirable manufacturing characteristics. The thermoplastic polyisoprene rubber balloon material may be utilized in a wide variety of balloon catheters, in addition to the single lumen balloon-tipped micro catheter of the present invention.

DETAILED DESCRIPTION OF THE INVENTION

The following detailed description should be read with reference to the drawings in which similar elements in different drawings are numbered the same. The drawings, which are not necessarily to scale, depict selected preferred embodiments and are not intended to limit the scope or spirit of the invention.

Figure 1:
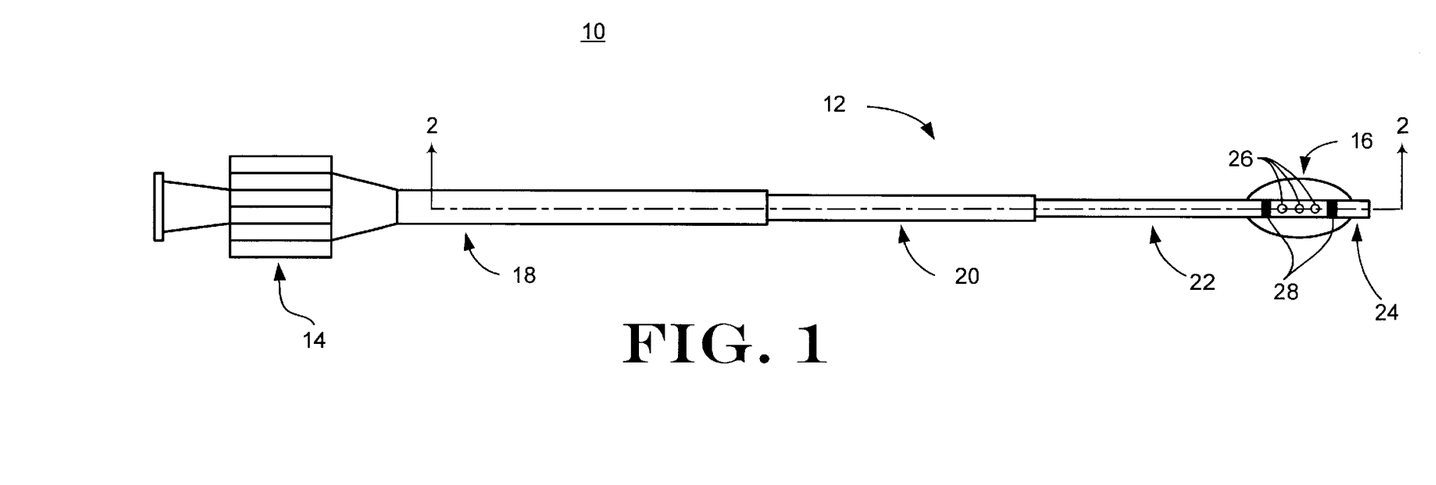
FIG. 1 is a plan view of a single lumen balloon-tipped micro catheter in accordance with an exemplary embodiment of the present invention.

Refer now to FIG. 1, which illustrates a single lumen balloon-tipped micro catheter 10 in accordance with an exemplary embodiment of the present invention. Micro catheter 10 includes an elongate shaft 12 with a hub 14 connected to its proximal end and a balloon 16 connected to its distal end. The hub 14 may be connected to a standard "Y" adapter (not shown), which in turn may be connected to a fluid source such as a syringe for inflating and deflating balloon 16. A guide wire (not shown) is insertable into the "Y" adapter, through the hub 14, through the shaft 12, and out the distal end of the catheter 10 adjacent the balloon 16.

The elongate shaft 12 includes a proximal portion 18, a mid portion 20, and a distal portion 22. The distal portion 22 is relatively more flexible than the proximal portion 18. The mid portion 20 is more flexible than the proximal portion 18 and less flexible than the distal portion 22 to provide a gradual transition in stiffness from the proximal end of the shaft 12 to the distal end of the shaft 12. The distal portion 22 of the shaft 12 extends into the balloon 16 to eliminate abrupt transitions in stiffness in the balloon region.

The distal portion 22 of the elongate shaft 12 includes a distal tip 24 containing a guide wire seal positioned adjacent the distal end of the balloon 16. The guide wire seal in the distal tip 24 forms a fluid-tight seal with the guide wire (not shown) inserted in the lumen (not visible) of the elongate shaft 12, and is discussed in more detail with reference to FIGS. 3A–3C. One or more inflation ports 26 are disposed on the distal portion 22 of the shaft 12 in alignment with the interior of the balloon 16 proximal of the guide wire seal in the distal tip 24. The inflation ports 26 provide a fluid path from the lumen of the shaft 12 to the interior of the balloon 16. The distal portion 22 of the shaft 12 also includes one or more radiopaque marker band(s) 28 to facilitate fluoroscopic visualization.

Figure 2:
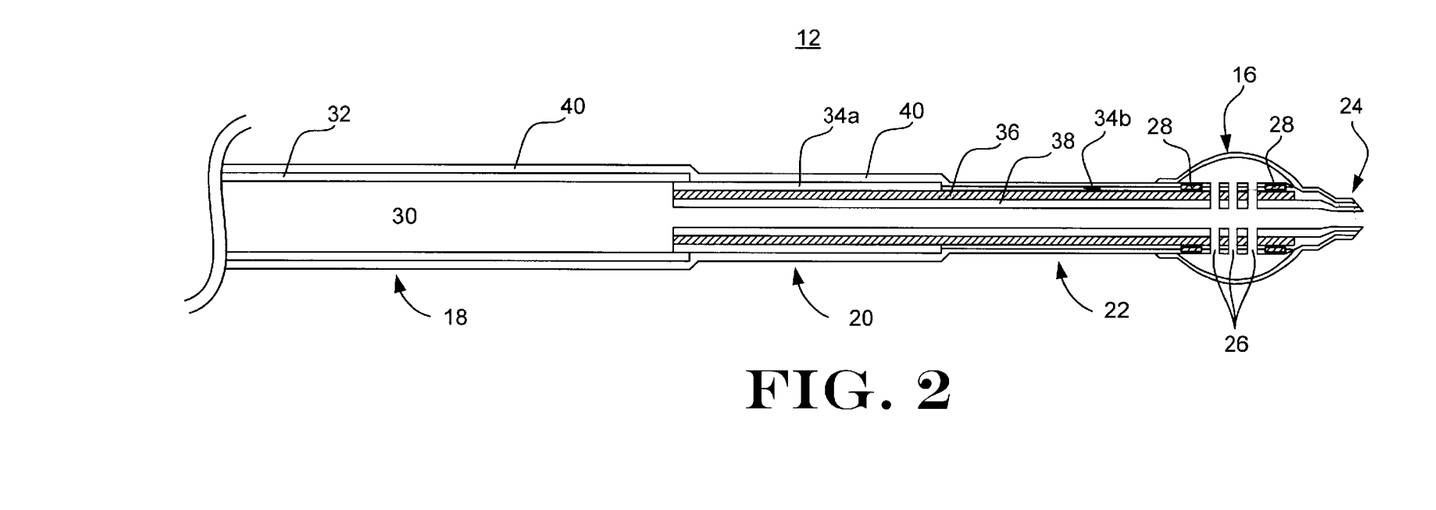
FIG. 2 is a longitudinal cross-sectional view, exaggerated in the radial direction, of the shaft and balloon of the micro catheter illustrated in FIG. 1.

Refer now to FIG. 2, which illustrates a longitudinal cross-sectional view taken along line 2—2 in FIG. 1, and which has been greatly exaggerated in the radial direction for purposes of illustration only. The proximal portion 18 of the elongate shaft 12 includes inner member 32. The mid portion 20 and distal portion 22 of the elongate shaft 12 include inner member 38. The mid portion 20 and the distal portion 22 of the shaft 12 also include an intermediate reinforcement layer 36 disposed over the inner layer 38. The mid portion 20 includes a relatively thick outer filler 34a and the distal portion 22 includes a relatively thin outer filler 34b disposed about the reinforcement layer 36. The inner layer 32 of the proximal portion 18 forms a lap joint with the outer filler layer 34a of the mid portion 20. Similarly, the outer filler layer 34a of the mid portion 20 forms a butt joint with the outer filler layer 34b and forms a lap joint with the reinforcement layer 36 and the inner layer 38 of the distal portion 22. An outer layer 40 in the form of a continuous integral tube overlays inner layer 32 and filler layers 34a and 34b.

The inner layer 32 of the proximal portion 18 may be formed of a relatively stiff medical grade polymer having a low co-efficient of friction such as polypropylene or high-density polyethylene. The outer filler layer 34a may be formed of a relatively stiff medical grade polymer such as polypropylene, high density polyethylene or low density polyethylene, but with a reduced outside diameter and/or wall thickness to impart more flexibility to the mid portion 20 relative to the proximal portion 18. Similarly, the outer filler layer 34b may be formed of a relatively flexible medical grade polymer such as high density polyethylene, low density polyethylene, or ultra low density polyethylene, but with a reduced outside diameter and/or wall thickness to impart more flexibility to the distal portion 22 relative to the mid portion 20.

The inner layer 38 of the distal portion 22 may be formed of a relatively flexible medical grade polymer having a low co-efficient or friction such as low density polyethylene or linear low density polyethylene. The reinforcement layer 36 may comprise a metallic or polymeric fiber structure such as a coil or braid. Preferably, the reinforcement layer 36 may comprise a metallic braid formed of a super elastic metal such as NITINOL. The outer layer 40 may be formed of a relatively flexible medical grade polymer such as ethylene vinylacetate (EVA), polyethylene or a blend of EVA and polyethylene. Preferably, the outer tubular layer 40 is formed of a heat shrinkable material to facilitate efficient manufacturing.

The overall length of the catheter 10 may be on the order of 150 cm, but may vary depending on the particular vascular site being treated. Assuming an overall length of 150 cm, the proximal portion 18 of the shaft 12 may have a length of approximately 120 cm including the length of the hub 14, the mid portion 20 of the shaft 12 may have a length of approximately 15 cm, and the distal portion 22 of the shaft 12 may have a length of approximately 15 cm including the portion of the shaft 22 extending through the balloon 16 and further including the distal tip 24.

The inside diameter of the shaft 12 must be sufficiently large to accommodate a conventional guide wire and allow for the passage of inflation fluid to inflate and deflate the balloon 16. Accordingly, the proximal portion 18 of the shaft 12 may have an inside diameter of approximately 0.020 inches, the mid portion 20 of the shaft 12 may have an inside diameter of approximately 0.016 inches, and the distal portion 22 of the shaft 12 may have an inside diameter of approximately 0.016 inches when the catheter 10 is used in combination with a conventional guide wire having an outside diameter of approximately 0.010 inches.

The outside diameter of the shaft 12 must be sufficiently small to navigate the vascular system and access the desired target site. For intracranial applications, for example, the outside diameter of the proximal portion 18 may be approximately 0.039 inches, the outside diameter of the mid portion 20 may be approximately 0.035 inches, and the outside diameter of the distal portion 22 may be approximately 0.032 inches.

The overall wall thickness of the proximal portion 18, mid portion 20, and distal portion 22 of the shaft 12 may be approximated from the inside and outside diameters given above. By way of example, not limitation, the inner layer 32 may have a wall thickness of approximately 0.0035 inches, the outer filler layer 34a may have a wall thickness of approximately 0.001 inches, the outer filler layer 34b may have a wall thickness of approximately 0.0075 inches, and the inner layer 38 may have a wall thickness of approximately 0.001 inches. The overall thickness of the reinforcement layer 36 is a function of the size of the individual filaments of the reinforcement structure, but generally may be on the order of 0.001 inches. The outer layer 40 may have a wall thickness on the order of 0.003 inches to 0.004 inches, which generally increases from the proximal end to the distal end if a heat shrink tubing have a uniform initial wall thickness is utilized.

As mentioned previously, the reinforcement layer 36 may comprise a metallic braid of super elastic metal such as NITINOL. Such a NITINOL braid structure may comprise 8 filaments braided in a pattern wherein one wire alternatively passes under and over every wire. Alternatively, the braid structure may comprise 16 filaments braided in a pattern wherein each wire passes alternatively under and over two wires. Preferably, the individual metallic filaments have a rectangular cross-section with a height of approximately 0.0005 inches and a width of approximately 0.003 inches to minimize the wall thickness of the reinforcement layer 36.

Inflatable balloon 16 may be formed of a wide variety of suitable compliant or non-compliant materials known in the art. However, for purposes of aneurysm reformation, elastomeric polymers are preferred. Examples of suitable elastomers include silicone, latex, and thermoplastic polyolefin rubbers. Alternatively, the balloon 16 may be formed of a thermoplastic polyisoprene rubber such as hydrogenated polyisoprene in accordance with the present invention. Thermoplastic polyisoprene rubber has a number of advantages in terms of both performance and manufacture over conventional elastomeric materials.

For example, silicone balloons tend to yield larger profiles due to manufacturing limitations associated with wall thickness. In addition, silicone balloons are expensive to manufacture and assemble because they require specialized manufacturing equipment and are not easily bonded to conventional shaft materials. Similarly, latex balloons are difficult to bond to conventional shaft materials. Latex balloons are considered toxic and excessively compliant for most intravascular applications. Balloons formed of thermoplastic polyolefin rubbers typically have a larger profile due to manufacturing limitations associated with wall thickness. Specifically, thermoplastic polyolefin rubbers usually contain a dispersion of EPDM rubber which limits how thin the balloon tubing may be extruded.

By contrast, balloons formed of thermoplastic polyisoprene rubber such as hydrogenated polyisoprene have superior performance and manufacturing attributes. For example, hydrogenated polyisoprene, which is commercially available under the trade name CHRONOPRENE from CT Biomaterials, may be processed with standard polyolefin processing equipment to obtain balloon tubing having a wall thickness of approximately 0.003 inches to 0.010 inches and a corresponding inside diameter of approximately 0.016 inches to 0.028 inches. Such balloon tubing has been demonstrated to produce balloons having a nominal outside diameter when inflated of approximately 3.0 mm to 5.5 mm. The wall thickness of the balloon is on the order of 0.001 inches, which allows the balloon to have a very low deflated profile, which in turn allows for access to narrow vasculature.

Balloons made from thermoplastic polyisoprene rubber have been demonstrated in animal studies to conform easily to tortuous vascular geometry (e.g., vessel bends) during inflation. Such balloons inflate uniformly and typically form a cylindrical shape when inflated. The rupture pressure has been shown to be approximately one atmosphere, which is desirable for aneurysm reformation. Upon rupture, the balloon tends to form a longitudinal split or a tear at the distal bond site. These failure modes are preferable to minimize the risk of prolapsing the balloon and/or forming an embolism due to severed balloon fragments. The thermoplastic polyisoprene rubber has also demonstrated superior manufacturing capabilities. Hydrogenated polyisoprene is readily bondable to conventional shaft materials and may be extruded using conventional extrusion equipment.

Radiopaque marker bands 28 may be formed of a platinum iridium alloy in the form of a short tubular segment having an inside diameter conforming to the reinforcement layer 36 and an outside diameter large enough to provide fluoroscopic visibility but small enough to minimize the corresponding increase in profile. Preferably, two radiopaque marker bands 28 are provided at either end of the inflatable portion of the balloon 16 such that the inflatable portion of the balloon may be properly positioned at the treatment site with the assistance with x-ray fluoroscopy. Those skilled in the art will recognize that any number of radiopaque marker bands formed of a wide variety of radiopaque materials may be utilized for the same purpose.

Alternatively, the radiopaque marker bands 28 may be eliminated by providing a radiopaque polymer tube laminated over the outer layer 40 under the balloon 16. Specifically, a thin polymer tube loaded with a radiopaque agent such as a tungsten-filled polyethylene tube may be laminated over the outer layer 40 in alignment with the inflatable portion of the balloon 16. Such a radiopaque loaded tube would serve the same purpose as the marker bands 28, but would provide three distinct advantages. First, the radiopaque loaded tube would act as a low-friction interface with the balloon 16 to prevent the balloon 16 from sticking to the outer layer 40. Second, the radiopaque loaded tube would be substantially more flexible than a metallic marker band. Third, the radiopaque loaded tube would be continuous from the proximal end of the balloon to the distal end of the balloon such that abrupt transitions in stiffness would be eliminated. Accordingly, such a radiopaque tube would act in concert with the distal portion 22 of the shaft 12 to eliminate all abrupt transitions in stiffness in the balloon region.

Figure 3A:
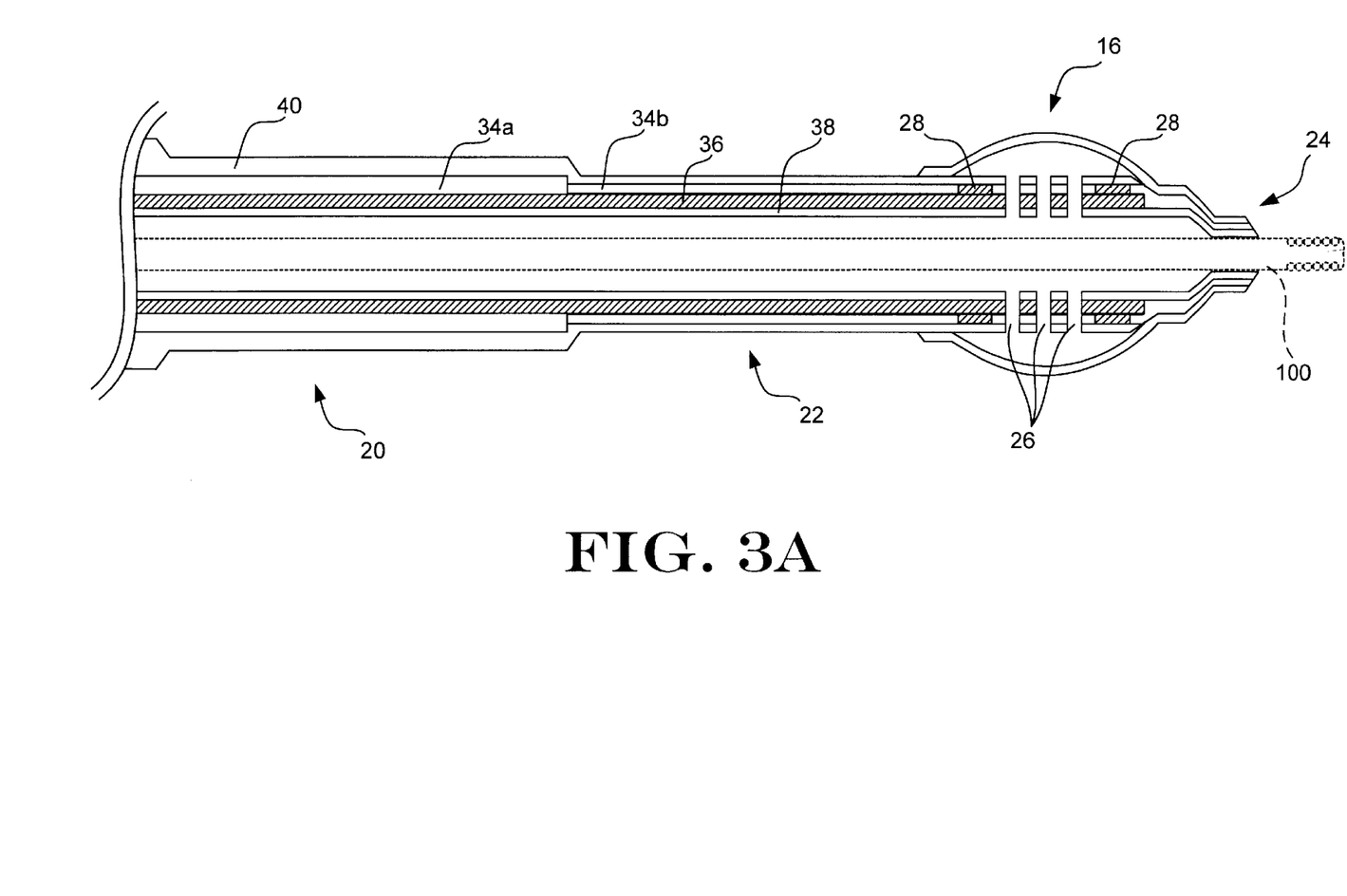
FIG. 3A is an enlarged detailed longitudinal cross-sectional view of a first embodiment the distal portion of the shaft and balloon of the micro catheter illustrated in FIG. 1.

Refer now to FIG. 3A, which illustrates an enlarged detailed longitudinal cross-sectional view of the distal portion 22 of the shaft 12 and the balloon 16 region of the catheter 10. As stated previously, distal portion 22 includes a distal tip 24 containing a seal which forms a fluid-tight seal about the guide wire 100 (shown in phantom). The guide wire may be a tolerance type seal or an interference type seal. A tolerance type seal provides, a gap between the interior of the tip 24 and the guide wire 100 that is sufficiently small to inhibit the loss of inflation fluid therethrough. An interference type seal does not provide a gap, but rather provides a contact area between the inside surface of the tip 24 and the guide wire 100 that inhibits the loss of inflation fluid. Preferably, an interference seal is utilized wherein the tip 24 inside diameter is approximately 0.00950 inches to 0.00995 inches for use with a guide wire 100 having an outside diameter of 0.0100 inches. With either a tolerance or interference type seal, a fluid tight seal is provided between the tip 24 and the guide wire 100 such that fluid introduced into the lumen 30 of the shaft 12 passes through the annular space between the inside surface of the shaft 12 and the outside surface of the guide wire 100, through the inflation ports 26, and into the interior of the balloon 16. With this arrangement, the balloon 16 may be inflated via the lumen 30 of the elongate shaft 12 without the necessity of a separate inflation lumen.

The seal may be formed by a reduced inside diameter region of the distal tip 24. Specifically, the seal may be formed by thermally reforming the various layers of the tip 24 distal of the balloon 16 in addition to the distal waist of the balloon 16 to form a relatively soft atraumatic tip having a reduced inside diameter corresponding to the outside diameter of the guide wire 100. The reinforcement layer 36 terminates short of the tip 24 to form a soft compliant tip such that the seal may elastically expand to accommodate the guide wire 100.

Inflation ports 26 comprise holes through the inner layer 38, the reinforcement layer 36, and the outer layer 40. Preferably, the inflation ports 26 are positioned between the individual filaments of the reinforcement layer 36. Also preferably, several inflation ports are utilized having an inside diameter sufficiently large to readily inflate and deflate the balloon 16. Those skilled in the art will recognize that a wide variety of inflation ports having different sizes and shapes may be utilized to serve the same purpose.

Figure 3B:
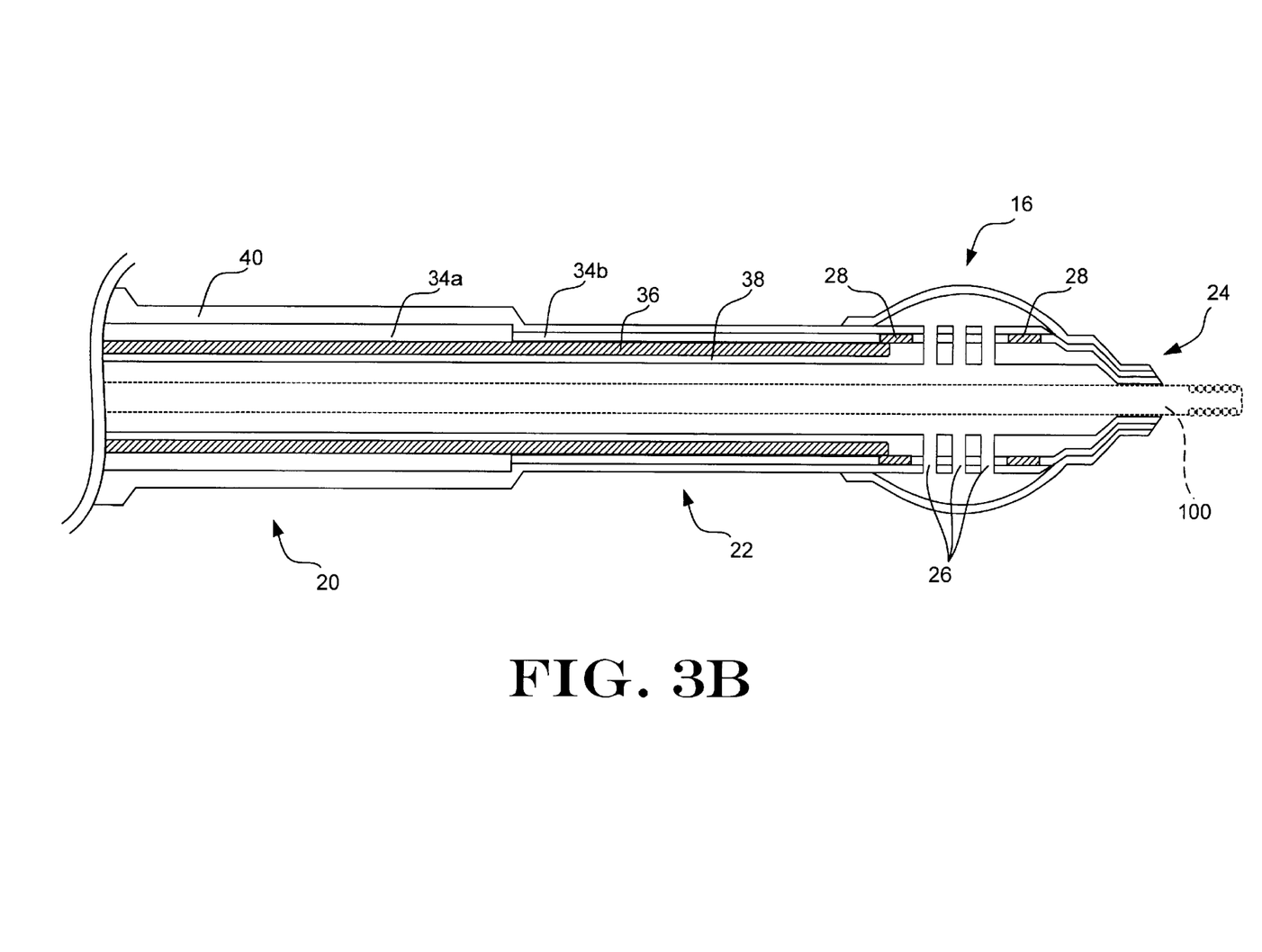
FIG. 3B is an enlarged detailed longitudinal cross-sectional view of a second embodiment the distal portion of the shaft and balloon of the micro catheter illustrated in FIG. 1.

Refer now to FIG. 3B, which illustrates an enlarged detailed longitudinal cross-sectional view of an alternative embodiment of the distal portion 22 of the shaft 12 and the balloon 16 region of the catheter 10. Except as described herein, the distal portion 22 illustrated in FIG. 3B is the same in form and function as described with reference to FIG. 3A.

In this alternative embodiment, the reinforcement layer 36 does not extend into the balloon 16 region, but rather terminates adjacent the proximal end of the balloon 16. Terminating the reinforcement layer adjacent the proximal end of the balloon 16 provides a smooth transition between the shaft 12 and the balloon 16, particularly with the reinforcement layer terminating at the proximal waist of the balloon 16. The proximal waist of the balloon 16 tends to be relatively stiff as compared to the remainder of the balloon 16, and thereby causes an increase in stiffness of the shaft 12 adjacent the proximal waist. The increase in stiffness adjacent the proximal waist of the balloon 16, absent the reinforcement layer 36, may have a tendency to cause the shaft 12 to kink. By terminating the reinforcement layer 36 adjacent the proximal waist of the balloon 16, the reinforcement layer acts as a strain relief across the proximal waist of the balloon 16, thereby reducing the probability of the shaft 12 kinking adjacent thereto.

Figure 3C:
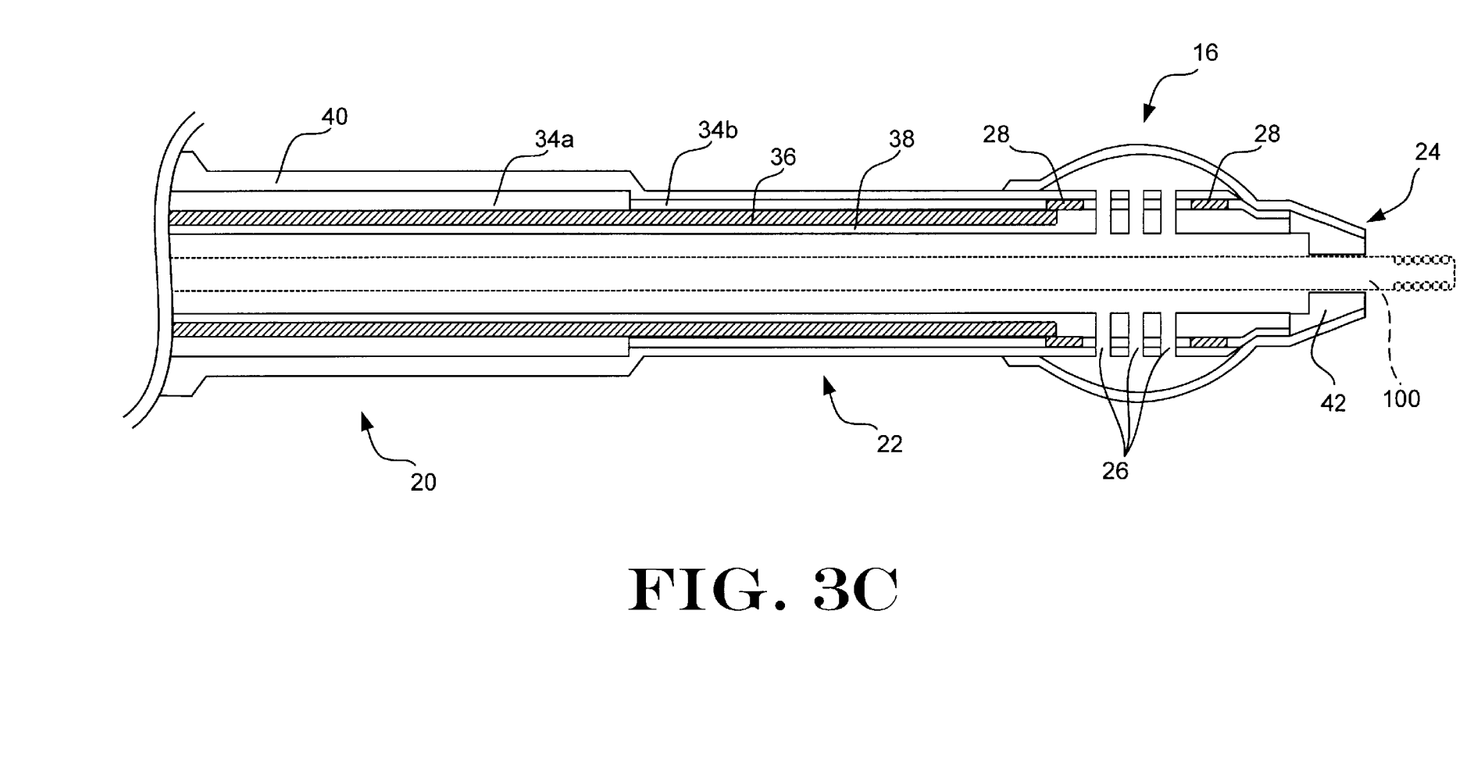
FIG. 3C is an enlarged detailed longitudinal cross-sectional view of a third embodiment the distal portion of the shaft and balloon of the micro catheter illustrated in FIG. 1.

Refer now to FIG. 3C, which illustrates an enlarged detailed longitudinal cross-sectional view of an alternative embodiment of the distal portion 22 of the shaft 12 and the balloon 16 region of the catheter 10. Except as described herein, the distal portion 22 illustrated in FIG. 3C is the same in form and function as described with reference to FIG. 3B.

In this alternative embodiment, the distal tip 24 comprises an extension of the distal waist of the balloon 16 and a relatively soft polymer segment 42. The polymer segment 42 is butt welded to the distal inner layer 38 and the outer filler layer 34b which terminate proximal of the distal tip 24. The polymer segment 42 and the distal waist of the balloon 16 may be heat formed to the desired size and shape of the tip 24. The polymer segment 42 may have an inside diameter to form an interference seal as discussed previously and may be formed of linear low density polyethylene, low density polyethylene, ultra low density polyethylene or other like material. The polymer segment 42 provides a softer tip 24 than would otherwise have been achieved by extending the distal inner layer 38 and the outer filler layer 34b, thus providing an extremely soft distal tip 24.

Catheter 10 may be manufactured using a number of conventional techniques, as will be appreciated by those skilled in the art. Preferably, however, the micro catheter 10 is is manufactured utilizing the following procedure. Prefabricated inner tubular layer 32 and outer filler layer 34a (with reinforcement layer 36 and inner layer 38) are thermally bonded to form a lap joint having a length of approximately 0.2 mm to 5.0 mm. The radiopaque marker bands 28 are then placed over the reinforcement layer 36 at the position where the balloon 16 will be attached. The outer layer 40 in the form of a heat-shrink tube is then placed over the inner layer 32, the outer filler layers 34a and 34b, and the radiopaque marker bands 28, and subsequently exposed to heat. The heat causes the outer layer 40 to shrink onto the inner layer 32 and the outer filler layers 34a and 34b to form a shaft subassembly. A plurality of inflation ports 26 are punched, drilled, or other wise formed through the distal portion 22 of the shaft 12 between the radiopaque marker bands 28. The balloon 16 is then positioned over the distal portion 22 of the shaft 12 adjacent the radiopaque marker bands 28. The proximal and distal ends of the balloon 16 are thermally bonded to the outer layer 40 using known techniques.

The distal tip 24 is then formed by thermally reforming the distal end of the balloon 16, the distal end of the outer layer 40, and the distal end of the inner layer 38 using heat, pressure, and tension. Alternatively, if a polymer segment 42 is utilized in place of extending the various layers of the shaft 12, the polymer segment 42 is butt welded to the distal end of the shaft 12, and the distal end of the balloon 16 and polymer segment 42 are thermally reformed to the desired size and shape. The tip 24 is preferably reformed to have an inside diameter sized to provide an interference seal as discussed previously. The seal contained in the distal tip 24 may alternatively be formed by placing a radiopaque marker band (having a smaller inside diameter than bands 28) in the distal end of the inner layer 38 so as to form a reduced diameter section to form a fluid tight seal with the guide wire 100. The tip 24 may extend approximately 1 mm to 5 mm beyond the distal end of the balloon 16 to form an atraumatic tip. In certain applications, an extended distal tip 24 of approximately 10 mm to 20 mm beyond the distal end of the balloon 16 may be utilized to improve stability of the catheter 10 as it is advance over the guide wire 100.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A single lumen balloon-tipped micro catheter for use in combination with a movable guide wire, comprising:

an elongate shaft having a proximal portion, a mid portion, a distal portion, and a lumen extending therethrough, the distal portion comprising a reinforcement layer disposed between an inner polymer layer and an outer polymer layer, the reinforcement layer defining a reinforced region of the shaft, the reinforcement layer terminating proximal of a distal end of the inner and outer layers to define an unreinforced region of the shaft;

an inflatable balloon having a proximal end, a distal end, and an interior, the proximal and distal ends of the balloon connected to the distal portion of the shaft such that the reinforcement layer of the distal portion of the shaft extends into the interior of the balloon to thereby eliminate significant transitions in stiffness;

an inflation port extending through the distal portion of the shaft to provide a fluid path between the lumen of the shaft and the interior of the balloon; and a seal connected to the distal portion of the shaft distal of the inflation port, the seal having a lumen sized to form a fluid seal with the movable guide wire disposed therein.

2. A micro catheter as in claim 1, wherein a plurality of inflation ports extend through the distal portion of the shaft.

3. A micro catheter as in claim 2, wherein the reinforcement layer comprises a braid, and the inflation ports are disposed between filaments of the braid.

4. A micro catheter as in claim 3, wherein the filaments are formed of a super elastic metal.

5. A micro catheter as in claim 4, further comprising a radiopaque marker band disposed between the inner and outer polymer layers adjacent the balloon.

6. A micro catheter as in claim 1, further comprising a radiopaque loaded polymer layer disposed over the outer layer adjacent the balloon.

7. A micro catheter as in claim 1, wherein the outer layer of the distal portion of the shaft includes a lubricious coating thereon, except at locations where the balloon is connected thereto.

8. A micro catheter as in claim 1, wherein the seal is formed by a reduced diameter portion of the distal portion of the shaft.

9. A micro catheter as in claim 1, wherein the seal is sized to form an interference fit with the guide wire.

10. A micro catheter as in claim 1, wherein the seal is formed of a non-elastomer.

11. A micro catheter as in claim 1, wherein the proximal portion of the shaft includes a relatively stiff tube and the mid portion of the shaft includes a relatively flexible tube.

12. A micro catheter as in claim 1, wherein the proximal portion and the mid portion of the shaft include an outer sleeve.

13. A micro catheter as in claim 12, wherein the outer sleeve and the outer layer of the distal portion of the shaft comprise an integral tube.

14. A micro catheter as in claim 1, wherein the balloon is formed of an elastomeric polymer.

15. A micro catheter as in claim 14, wherein the elastomeric polymer comprises a thermoplastic polyisoprene rubber.

16. A micro catheter as in claim 15, wherein the thermoplastic polyisoprene rubber comprises hydrogenated polyisoprene.

17. A balloon catheter as in claim 1, further comprising a soft polymer segment connected to a distal end of the distal shaft portion and extending beyond the distal end of the distal shaft portion to define an atraumatic tip.

18. A single lumen balloon-tipped micro catheter as in claim 1, wherein the distal end of the balloon is connected to the unreinforced region of the shaft.

19. A single lumen balloon-tipped micro catheter as in claim 18, wherein the proximal end of the balloon is connected to the reinforced region of the shaft.

* * * * *

UNITED STATES PATENT AND TRADEMARK OFFICE
CERTIFICATE OF CORRECTION

PATENT NO. : 6,648,854 B1
DATED : November 18, 2003
INVENTOR(S) : Marlowe E. Patterson et al.

It is certified that error appears in the above-identified patent and that said Letters Patent is hereby corrected as shown below:

<u>Column 10,</u>
Line 11, delete "as in claim 1", and insert therefor -- as in claim 11 --.

Signed and Sealed this

Sixth Day of July, 2004

JON W. DUDAS
*Acting Director of the United States Patent and Trademark Office*